US011234674B2

(12) United States Patent
Cho et al.

(10) Patent No.: US 11,234,674 B2
(45) Date of Patent: Feb. 1, 2022

(54) METHOD AND ULTRASOUND APPARATUS FOR DISPLAYING LOCATION INFORMATION OF BURSA

(71) Applicants: SAMSUNG MEDISON CO., LTD., Gangwon-do (KR); SAMSUNG ELECTRONICS CO., LTD., Suwon-si (KR)

(72) Inventors: Eun-mi Cho, Gangwon-do (KR); Jung-taek Oh, Seoul (KR)

(73) Assignees: SAMSUNG MEDISON CO., LTD., Gangwon-Do (KR); SAMSUNG ELECTRONICS CO., LTD., Suwon-si (KR)

( * ) Notice: Subject to any disclaimer, the term of this patent is extended or adjusted under 35 U.S.C. 154(b) by 1444 days.

(21) Appl. No.: 14/601,165

(22) Filed: Jan. 20, 2015

(65) Prior Publication Data

US 2015/0238164 A1 Aug. 27, 2015

(30) Foreign Application Priority Data

Feb. 26, 2014 (KR) .......................... 10-2014-0022889

(51) Int. Cl.
*A61B 8/08* (2006.01)
*A61B 8/14* (2006.01)
(Continued)

(52) U.S. Cl.
CPC ............ *A61B 8/0858* (2013.01); *A61B 8/085* (2013.01); *A61B 8/14* (2013.01); *A61B 8/469* (2013.01);
(Continued)

(58) Field of Classification Search
CPC ..... A61B 8/0858; A61B 8/085; A61B 8/5215; A61B 8/14; A61B 8/469; A61B 5/4576; A61B 8/565; A61B 8/463; A61B 8/0841
See application file for complete search history.

(56) References Cited

U.S. PATENT DOCUMENTS 8,313,437 B1 11/2012 Suri
2003/0171668 A1 9/2003 Tsujino et al.
(Continued)

FOREIGN PATENT DOCUMENTS

CN 102639062 A 8/2012
EP 2441392 A1 4/2012
(Continued)

OTHER PUBLICATIONS

Daenen et al (Ultrasound Of The Shoulder, JBR-BTR, 2007, 90: 325-337) (Year: 2007).*
(Continued)

*Primary Examiner* — Serkan Akar
(74) *Attorney, Agent, or Firm* — Morgan, Lewis & Bockius LLP (57) ABSTRACT

Provided is a method of displaying location information of a bursa, which includes: obtaining shoulder ultrasound image data; detecting a fat layer located between a deltoid muscle and a tendon, based on information about an intensity of an echo signal contained in the shoulder ultrasound image data; detecting the bursa located between the fat layer and the tendon by using a location of the fat layer; and displaying the location information of the bursa on a shoulder ultrasound image generated based on the shoulder ultrasound image data.

12 Claims, 9 Drawing Sheets

(51) Int. Cl.
  *A61B 8/00* (2006.01)
  *A61B 5/00* (2006.01)
(52) U.S. Cl.
  CPC .......... *A61B 8/5215* (2013.01); *A61B 5/4576* (2013.01); *A61B 8/0841* (2013.01); *A61B 8/463* (2013.01); *A61B 8/565* (2013.01)

(56) References Cited

U.S. PATENT DOCUMENTS

| | | |
|---|---|---|
| 2004/0193048 A1 | 9/2004 | Tsoref |
| 2005/0020918 A1* | 1/2005 | Wilk .................... A61B 5/6804 600/439 |
| 2007/0073145 A1 | 3/2007 | Fan et al. |
| 2011/0082372 A1* | 4/2011 | Tateyama ............. A61B 8/0833 600/443 |
| 2012/0116219 A1 | 5/2012 | Miller et al. |
| 2012/0215109 A1 | 8/2012 | Kubota et al. |
| 2013/0000654 A1 | 1/2013 | Osinenko |
| 2013/0006549 A1 | 1/2013 | Gronseth et al. |
| 2013/0096471 A1* | 4/2013 | Slayton .................. A61B 8/14 601/3 |
| 2013/0178740 A1 | 7/2013 | Han |
| 2014/0187944 A1 | 7/2014 | Slayton et al. |
| 2015/0141822 A1 | 5/2015 | Miyauchi et al. |

FOREIGN PATENT DOCUMENTS

| | | |
|---|---|---|
| JP | 2985147 B2 | 11/1999 |
| JP | 2010-148548 A | 7/2010 |
| JP | WO 2010/143588 A1 | 11/2012 |
| KR | 10-2013-0080640 A | 7/2013 |
| KR | 2013-0080477 A | 7/2013 |
| WO | 2013/101562 A2 | 7/2013 |
| WO | 2013/183432 A1 | 12/2013 |

OTHER PUBLICATIONS

European Search Report dated Jul. 16, 2015 issued in European Patent Application No. 14200598.2.
M. Holsbeeck, et al., "Sonography of the Shoulder: Evaluation of the Subacromial-Subdeltoid Bursa," American Journal of Roentgenology, vol. 160, No. 3, Mar. 1, 1993, pp. 561-564.
Y. Tsai, et al., "Detection of Subacrominal Bursa Thickening by Sonography in Shoulder Impingement Syndrome," Chang Gung Medical Journal, Mar. 1, 2007, pp. 135-141.
H. Kim, et al., "Ultrasonographic findings of painful shoulders and correlation between physical examination and ultrasonographic rotator cuff tear," Modern Rheumatology, Official Journal of the Japan College of Rheumatology, Springer-Verlag, Jun. 20, 2007, vol. 17, No. 3, pp. 213-219.
Ian Beggs, "Shoulder Ultrasound," Seminars in Ultrasound CT and MRi, 2011, pp. 101-113.
First Office Action issued in Chinese Application No. 201510085020.8 dated Nov. 2, 2018, with English translation.
Korean Office Action dated May 27, 2020 issued in Korean Patent Application No. 10-2014-0022889 (with English translation).
Korean Notice of Allowance dated Jan. 19, 2021 issued in Korean Patent Application No. 10-2014-0022889 (with English translation).

* cited by examiner

METHOD AND ULTRASOUND APPARATUS FOR DISPLAYING LOCATION INFORMATION OF BURSA

RELATED APPLICATIONS

This application claims the benefit of Korean Patent Application No. 10-2014-0022889, filed on Feb. 26, 2014, in the Korean Intellectual Property Office, the disclosure of which is incorporated herein in its entirety by reference.

BACKGROUND

1. Field

One or more embodiments of the present invention relate to a method and ultrasound apparatus for displaying location information of a bursa on an ultrasound image.

2. Description of the Related Art

An ultrasound diagnosis device transmits ultrasound signals from a body surface of an object toward a predetermined portion inside a body and uses information of ultrasound signals reflected from tissue in the body to obtain tomographic images of soft tissue or blood flow.

Such an ultrasound diagnosis device is compact, inexpensive, and enables real-time display of ultrasound images. Furthermore, an ultrasound diagnosis device causes no exposure to radiation such as X-rays, thus being highly safe. Therefore, ultrasound diagnosis devices have been widely used together with other types of imaging diagnosis devices, including X-ray diagnosis devices, computerized tomography (CT) scanners, magnetic resonance imaging (MRI) devices, nuclear medical diagnosis devices, etc.

SUMMARY

One or more embodiments of the present invention include a method and ultrasound apparatus for displaying location information of a bursa on a shoulder ultrasound image so that a user may accurately identify a location of the bursa in the shoulder ultrasound image.

Additional aspects will be set forth in part in the description which follows and, in part, will be apparent from the description, or may be learned by practice of the presented embodiments.

According to one or more embodiments of the present invention, a method of displaying location information of a bursa includes: obtaining shoulder ultrasound image data; detecting a fat layer located between a deltoid muscle and a tendon, based on information about an intensity of an echo signal contained in the shoulder ultrasound image data; detecting the bursa located between the fat layer and the tendon by using a location of the fat layer; and displaying the location information of the bursa on a shoulder ultrasound image generated based on the shoulder ultrasound image data.

The detecting of the fat layer may include: selecting a region of interest (ROI) including the deltoid muscle and the tendon in the shoulder ultrasound image, based on a user input; and detecting the fat layer based on the information about the intensity of the echo signal reflected from the ROI.

The method may further include changing a location or size of the ROI based on the location of the fat layer or the bursa. The detecting of the fat layer may include detecting a region having the intensity of the echo signal that is greater than or equal to a threshold value as the fat layer.

The detecting of the fat layer may include: detecting a first boundary having an intensity gradient of the echo signal that is greater than or equal to a positive first threshold in the shoulder ultrasound image; and determining the first boundary as an upper edge of the fat layer.

The detecting of the fat layer may further include: detecting a second boundary having an intensity gradient of the echo signal that is less than or equal to a negative second threshold in the shoulder ultrasound image; and determining the second boundary as a lower edge of the fat layer.

The detecting of the fat layer may further include detecting a thickness of the fat layer based on a distance between the first and second boundaries.

The detecting of the bursa may include determining an anechoic zone disposed below the detected fat layer as the bursa.

The displaying of the location information of the bursa further may include: detecting a third boundary having an intensity gradient of the echo signal that is less than the positive first threshold and is greater than a third threshold in the shoulder ultrasound image; and determining the third boundary as an upper edge of the tendon.

The displaying of the location information of the bursa may further include detecting a thickness of the bursa based on a distance between the second and third boundaries.

The displaying of the location information of the bursa may include displaying an indicator having a preset shape at a location of the bursa on the shoulder ultrasound image.

The displaying of the location information of the bursa may include marking a first boundary line that distinguishes the bursa from the fat layer and a second boundary line that distinguishes the bursa from the tendon.

The displaying of the location information of the bursa may include: obtaining shoulder ultrasound image data in real-time during injection of a medicine into the bursa through a syringe; and displaying the location information of the bursa on a real-time shoulder ultrasound image by using the shoulder ultrasound image data obtained in real-time.

According to one or more embodiments of the present invention, an ultrasound apparatus includes: an ultrasound image data obtainer configured to obtain shoulder ultrasound image data; a controller configured to detect a fat layer located between a deltoid muscle and a tendon, based on information about an intensity of an echo signal contained in the shoulder ultrasound image data, and detect a bursa located between the fat layer and the tendon by using a location of the fat layer; and a display configured to display location information of the bursa on a shoulder ultrasound image generated based on the shoulder ultrasound image data.

The ultrasound apparatus may further include a user input unit configured to receive an input for selecting a region of interest (ROI) including the deltoid muscle and the tendon in the shoulder ultrasound image, wherein the controller detects the fat layer based on the information about the intensity of the echo signal reflected from the ROI.

The controller may change a location or size of the ROI based on the location of the fat layer or the bursa.

The controller may detect a region having the intensity of the echo signal that is greater than or equal to a threshold value as the fat layer.

The controller may detect a first boundary having an intensity gradient of the echo signal that is greater than or equal to a positive first threshold in the shoulder ultrasound image and determine the first boundary as an upper edge of the fat layer.

The controller may further detect a second boundary having an intensity gradient of the echo signal that is less than or equal to a negative second threshold in the shoulder ultrasound image and determine the second boundary as a lower edge of the fat layer.

The controller may further detect a thickness of the fat layer based on a distance between the first and second boundaries.

The controller may determine an anechoic zone disposed below the detected fat layer as the bursa.

The controller may further detect a third boundary having an intensity gradient of the echo signal that is less than the positive first threshold and is greater than a third threshold in the shoulder ultrasound image and determine the third boundary as an upper edge of the tendon.

The controller may further detect a thickness of the bursa based on a distance between the second and third boundaries.

The display may display an indicator having a preset shape at a location of the bursa on the shoulder ultrasound image.

The display may display a first boundary line that distinguishes the bursa from the fat layer and a second boundary line that distinguishes the bursa from the tendon.

The ultrasound image data obtainer may obtain shoulder ultrasound image data in real-time during injection of a medicine into the bursa through a syringe, and the controller may control the display to display the location information of the bursa on a real-time shoulder ultrasound image by using the shoulder ultrasound image data obtained in real-time.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "ultrasonic image" refers to an image of an object obtained using an ultrasound signal. Furthermore, an object in the present specification may be a part of a body. For example, the object may include the liver, the heart, the brain, a breast, the abdomen, nuchal translucency (NT), shoulder muscles, and a fetus.

Furthermore, in the specification, an ultrasound image may vary in different forms. For example, the ultrasound image may include a brightness (B) mode image indicating the intensity of an ultrasound echo signal reflected from an object as brightness, a color Doppler image representing the speed of a moving object in color by using a Doppler effect, a spectral Doppler image showing a moving object as a spectrum by using a Doppler effect, a power Doppler image representing the intensity of a Doppler signal or the number of structures (e.g., red blood cells in blood) as colors, a motion (M) mode image showing movement of an object at a predetermined position over time, and an elasticity mode image indicating a difference between a reaction when compression is applied to a target object and a reaction when compression is not applied to the target object. In addition, according to an embodiment of the present invention, the ultrasound image may be a two-dimensional (2D), a three-dimensional (3D), or a four-dimensional (4D) image.

Furthermore, in the present specification, a "user" refers to a medical professional, such as a doctor, a nurse, a medical laboratory technologist, a sonographer, but the user is not limited thereto.

Exemplary embodiments of the present invention will now be described more fully hereinafter with reference to the accompanying drawings so that they may be easily implemented by one of ordinary skill in the art. However, the present embodiments may have different forms and should not be construed as being limited to the descriptions set forth herein. In addition, parts not related to the present invention are omitted to clarify the description of exemplary embodiments of the present invention. In the accompanying drawings, like reference numerals refer to like elements throughout.

Figure 1:
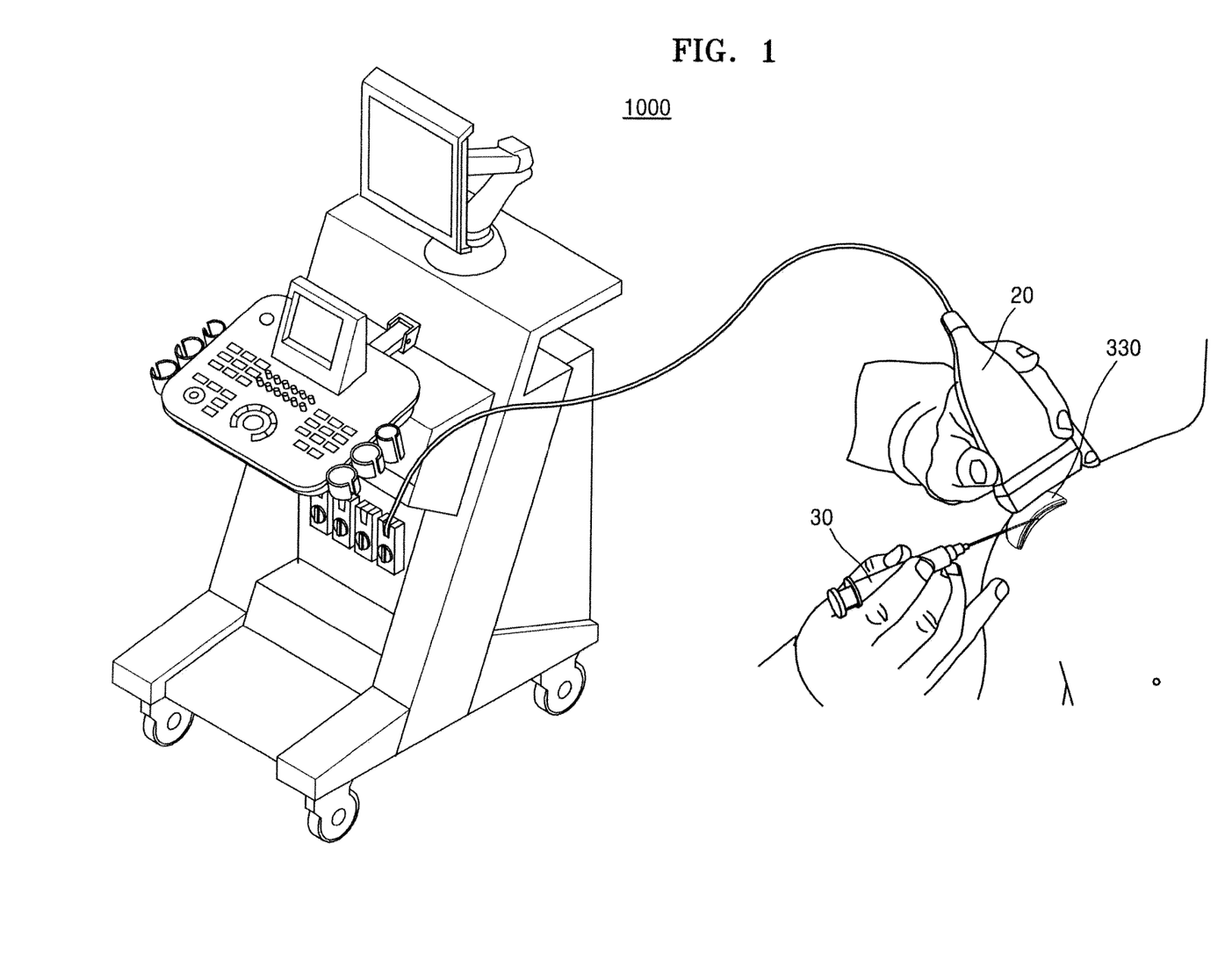
FIG. 1 illustrates an ultrasound apparatus according to an exemplary embodiment of the present invention.

FIG. 1 illustrates an ultrasound apparatus 1000 according to an exemplary embodiment of the present invention;

Referring to FIG. 1, the ultrasound apparatus 1000 may transmit an ultrasound signal to an object through a probe 20, receives an ultrasound echo signal (hereinafter, referred to as an 'echo signal') from the object through the probe 20, and generates an ultrasound image of the object.

For example, the ultrasound apparatus 1000 may transmit an ultrasound signal to an object that has a bursa 330, convert the intensity of an echo signal reflected from the object into a brightness value (e.g., 0 to 255), and generate a B mode image of the object that has the bursa 330.

In this case, since the bursa 330 is generally thinner than 2 mm, a user may have difficulty in accurately identifying a location of the bursa 330 in a B mode image. Furthermore, the bursa 330 may likely be confused with a muscle layer and a tendon layer.

In addition, if a medicine is not accurately injected into the bursa 330 through a syringe 30, the effect of treatment of the bursa 330 may be significantly reduced. Thus, there is a need for a system that easily distinguishes the bursa 330 in a shoulder ultrasound image.

A method of displaying location information of the bursa 330 on a shoulder ultrasound image in the ultrasound apparatus 1000 so that the user may easily identify the bursa 330 will now be described in detail with reference to FIG. 2.

Figure 2:
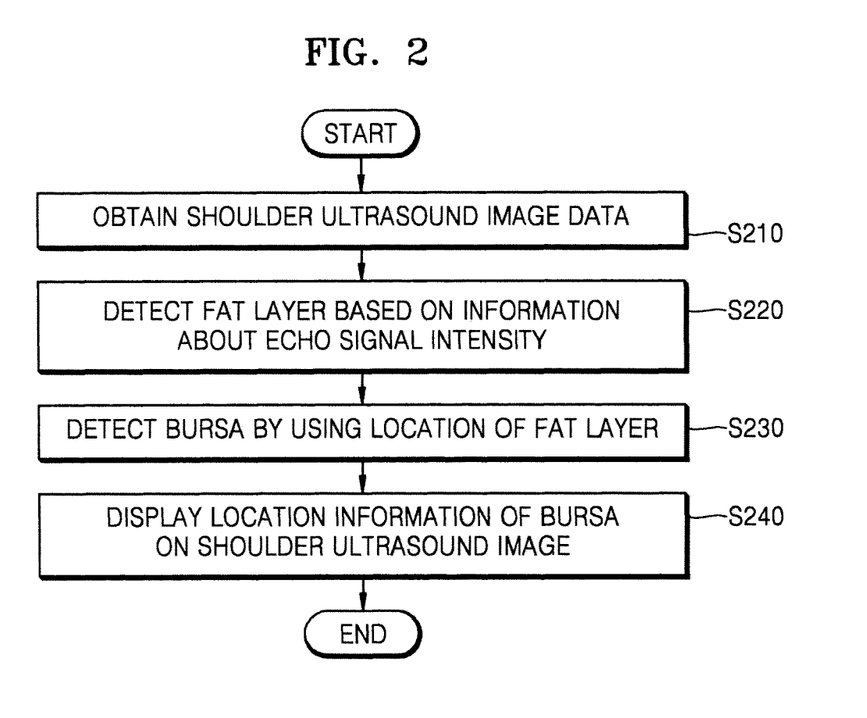
FIG. 2 is a flowchart of a method of displaying location information of a bursa in the ultrasound apparatus, according to an exemplary embodiment of the present invention.

FIG. 2 is a flowchart of a method of displaying location information of a bursa in the ultrasound apparatus 1000 of FIG. 1, according to an exemplary embodiment of the present invention.

The ultrasound apparatus 1000 may obtain shoulder ultrasound image data (S210). In one embodiment, the shoulder ultrasound image data may include brightness values (e.g., 0 to 255) of pixels, corresponding to the intensity of an echo signal that is reflected from an object.

For example, although a deltoid muscle generally has a low brightness value (e.g., less than or equal to 10), the deltoid muscle also includes internal parts which have brightness values that are greater than or equal to a first threshold (e.g., 50). Furthermore, a fat layer may have a brightness value that is greater than or equal to a second threshold (e.g., 150), and a bursa may have a low brightness value overall (e.g., less than or equal to 5). In this case, the second threshold may be greater than the first threshold. Since the fat layer has a high brightness value while the bursa has a low brightness value, the fat layer and the bursa may appear bright and dark in a shoulder ultrasound image, respectively.

In one embodiment, the ultrasound apparatus 1000 may directly generate the shoulder ultrasound image data or receive the shoulder ultrasound image data from the outside. For example, the ultrasound apparatus 1000 may generate shoulder ultrasound image data by transmitting an ultrasound signal to an object and receiving an echo signal reflected from the object. Alternatively, the ultrasound apparatus 1000 may receive shoulder ultrasound image data from an external server or device.

The ultrasound apparatus 1000 may detect a fat layer located between the deltoid muscle and a tendon, based on information about the intensity of an echo signal contained in the shoulder ultrasound image data (S220). According to an embodiment of the present invention, the information about the intensity of an echo signal may include the intensity of an echo signal corresponding to each pixel and an intensity gradient of the echo signal corresponding to a pixel, but is not limited thereto.

For example, the ultrasound apparatus 1000 may detect a region in which the intensity of an echo signal is greater than or equal to a threshold value (e.g., 150) as a fat layer. In general, among echo signals reflected from a deltoid muscle, a fat layer, a bursa, and a tendon, the echo signal reflected from the fat layer has the highest intensity. Thus, if the ultrasound apparatus 1000 analyzes shoulder ultrasound image data to detect a region having an echo signal intensity that is greater than or equal to a threshold value, the detected region may be a fat layer.

In one embodiment, the ultrasound apparatus 1000 may detect in a shoulder ultrasound image a first boundary where an intensity gradient of an echo signal is greater than or equal to a positive first threshold.

For example, the ultrasound apparatus 1000 may analyze the intensity of an echo signal in a direction that a depth value increases. The direction that a depth value increases may be a direction in which an ultrasound wave transmitted from the probe 20 propagates. Since a deltoid muscle and a fat layer in the shoulder ultrasound image generally have a low brightness value and a high brightness value, respectively, an intensity gradient may be greater than or equal to the first threshold at a boundary between the deltoid muscle and the fat layer.

Thus, the ultrasound apparatus 1000 may determine the first boundary having an echo signal intensity gradient that is greater than or equal to the positive first threshold as an upper edge of the fat layer or a lower edge of the deltoid muscle.

In addition, the ultrasound apparatus 1000 may detect in the shoulder ultrasound image a second boundary where an intensity gradient of an echo signal is less than or equal to a negative second threshold. For example, the ultrasound apparatus 1000 may analyze the intensity of an echo signal in a direction that a depth value increases. In this case, since a fat layer and a bursa in the shoulder ultrasound image generally have a high brightness value and a low brightness value, respectively, an intensity gradient may be less than or equal to the negative second threshold at a boundary between the fat layer and the bursa.

Thus, the ultrasound apparatus 1000 may determine the second boundary having an echo signal intensity gradient that is less than or equal to the negative second threshold as a lower edge of the fat layer or an upper edge of the bursa.

The ultrasound apparatus 1000 may also detect a thickness of a fat layer. For example, to do so, the ultrasound apparatus 1000 may measure a distance between the first boundary having an echo signal intensity gradient that is greater than or equal to the positive first threshold and the second boundary having an echo signal intensity gradient that is less than or equal to the negative second threshold. An operation of detecting the thickness of the fat layer, performed by the ultrasound apparatus 1000, will be described in more detail later with reference to FIG. 4.

The ultrasound apparatus 1000 may detect a bursa located between the fat layer and tendon by using a location of the fat layer (S230).

According to one embodiment, the ultrasound apparatus 1000 may determine an anechoic zone disposed below the fat layer as the bursa. For example, the ultrasound apparatus 1000 may determine a first anechoic zone disposed below an upper edge of the fat layer or a lower edge of the deltoid muscle as the bursa. Since an echo signal reflected from the bursa has a very low intensity, the bursa appears dark below the fat layer in the shoulder ultrasound image.

According to one embodiment, the ultrasound apparatus 1000 may detect a third boundary having an echo signal intensity gradient that is less than the positive first threshold and greater than a third threshold. For example, the ultrasound apparatus 1000 may analyze the intensity of an echo signal in a direction that a depth value increases. In this case, since the bursa has a very low brightness value and the tendon has a brightness value that is higher than the bursa and lower than the fat layer, an intensity gradient may be less than the positive first threshold and greater than the third threshold at a boundary between the bursa and the tendon.

Thus, the ultrasound apparatus 1000 may determine as an upper edge of the tendon or lower edge of the bursa the third boundary having an echo signal intensity gradient that is less than the positive first threshold and greater than the third threshold. Furthermore, the ultrasound apparatus 100 may also determine an anechoic zone located between the tendon and the fat layer as the bursa.

In addition, the ultrasound apparatus 1000 may detect a thickness of the bursa. For example, the ultrasound apparatus 1000 may detect the thickness of the bursa, based on a distance between the third boundary and the second boundary having an echo signal intensity gradient that is less than or equal to the negative second threshold. An operation of detecting the thickness of the bursa, performed by the ultrasound apparatus 1000, will be described in greater detail later with reference to FIG. 5

The ultrasound apparatus 1000 may display location information of the bursa on the shoulder ultrasound image, based on the shoulder ultrasound image data (S240).

For example, the ultrasound apparatus 1000 may display an indicator having a preset shape or color at a location of the bursa in the shoulder ultrasound image. The shape of the indicator may be preset by a user or the ultrasound apparatus 1000 (. The indicator having the preset shape may include an arrow, a triangle, a star shape, and a line, but is not limited thereto. The shape of the indicator may also vary according to a user's input.

In one embodiment, the ultrasound apparatus 1000 may display a first boundary line that distinguishes a bursa from a fat layer and a second boundary line that distinguishes a bursa from a tendon.

The ultrasound apparatus 1000 may also display a measured value such as a thickness of a bursa or fat layer. In this case, the measured value may be superimposed on the shoulder ultrasound image or displayed at a region that is separate from a region where the shoulder ultrasound image is displayed.

In addition, the ultrasound apparatus 1000 may provide location information of the bursa in real-time during injection of medicine into the bursa through a syringe. According to one embodiment, the ultrasound apparatus 1000 may provide location information of the bursa in real-time by repeatedly performing operations S210 through S240.

For example, while a medicine is being injected into the bursa through a syringe, the ultrasound apparatus 1000 may obtain shoulder ultrasound image data in real-time. To do so, the ultrasound apparatus 1000 may transmit an ultrasound signal to an object at predetermined time intervals and receive an echo signal from the object. In this case, the predetermined time interval at which the ultrasound apparatus 1000 obtains shoulder ultrasound image data may be set or changed by a user's input or a system of the ultrasound apparatus 1000.

The ultrasound apparatus 1000 may detect a fat layer based on an intensity gradient of an echo signal contained in the shoulder ultrasound image data obtained in real-time. The ultrasound apparatus 1000 may then detect a bursa based on a location of the fat layer. Since the operations of detecting the fat layer and the bursa are described above with reference to FIG. 2 (operations S220 and S230), detailed descriptions thereof are omitted herein. In this case, the ultrasound apparatus 1000 may display location information of the bursa on a real-time shoulder ultrasound image. The real-time shoulder ultrasound image may be an ultrasound image that is displayed in real-time by using the shoulder ultrasound image data obtained in real-time.

Figure 3:
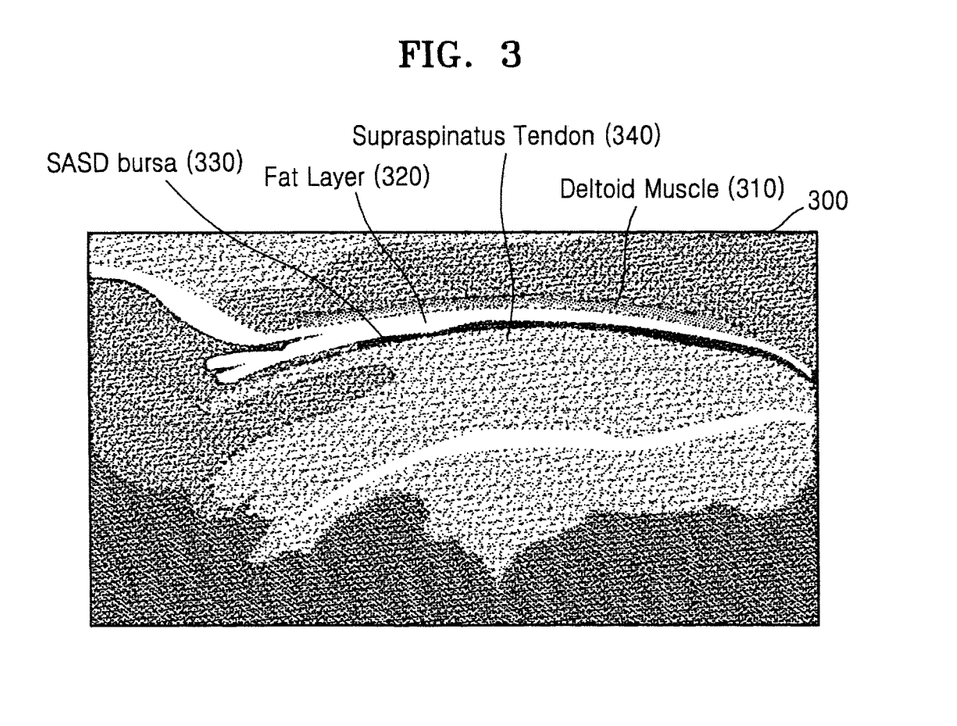
FIG. 3 illustrates a shoulder ultrasound image according to an exemplary embodiment of the present invention.

FIG. 3 illustrates a shoulder ultrasound image 300 according to an exemplary embodiment of the present invention;

Referring to FIG. 3, the ultrasound apparatus (1000 in FIG. 1) is configured to display the shoulder ultrasound image 300 based on shoulder ultrasound image data. In this case, the shoulder ultrasound image 300 shows a deltoid muscle 310, a fat layer 320, a subacromial-subdeltoid (SASD) bursa (hereinafter called a 'bursa') 330, and a supraspinatus tendon 340 that are sequentially displayed in a direction that a depth value increases.

As described above, although the deltoid muscle generally has a low brightness value (e.g., less than or equal to 10), the deltoid muscle 310 also includes regions that have brightness values that are greater than or equal to a first threshold (e.g., 50). Thus, an image of the deltoid muscle 310 is all dark with small white patterns in between.

Since the fat layer 320 has a brightness value that is greater than or equal to a second threshold (e.g., 150), an image of the fat layer may appear bright. Furthermore, the bursa 330 having a low brightness value overall may appear quite dark. Since the supraspinatus tendon 340 has a lower brightness value than the fat layer 320, an image of the supraspinatus tendon 340 may appear darker than the image of the fat layer 320. The brightest region located below the supraspinatus tendon 340 in the shoulder ultrasound image 300 may be bone.

The shoulder ultrasound image 300 will now be described in greater detail with reference to FIGS. 4 and 5.

Figure 4:
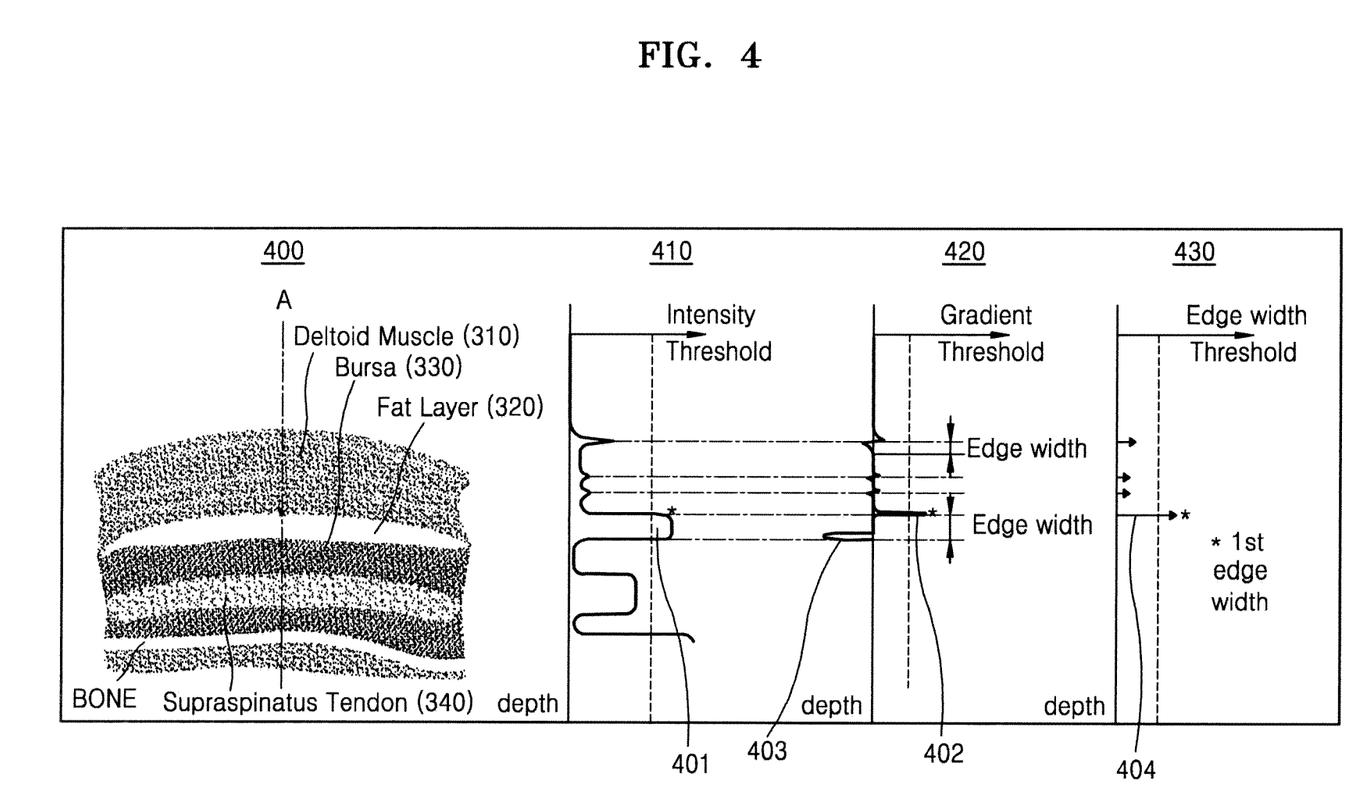
FIG. 4 illustrates detection of a fat layer and a bursa according to an exemplary embodiment of the present invention.

FIG. 4 illustrates detection of a fat layer 320 and a bursa 330 according to an exemplary embodiment of the present invention.

FIG. 4 illustrates a shoulder ultrasound image 400 that corresponds to a schematic diagram of the shoulder ultrasound image 300 of FIG. 3. A first graph 410 illustrates a result obtained by analyzing an echo signal along a reference axis A in a direction that a depth value increases.

As evident from the first graph 410, since the fat layer 320 has the highest echo signal intensity among the deltoid muscle 310, the fat layer 330, the bursa 330, and the supraspinatus tendon 340, the echo signal intensity of the fat layer 320 may be the first one that exceeds a threshold. The echo signal intensity then decreases sharply at the bursa 330 and increases again at the tendon layer 340. Thus, the ultrasound apparatus 1000 may determine a region 401 of the first graph 410 representing an intensity that is greater than or equal to the threshold as the fat layer 320.

A second graph 420 illustrates an echo signal intensity gradient (hereinafter called an 'intensity gradient') obtained by analyzing an echo signal along a reference axis A in a direction that a depth value increases. As evident from the second graph 420, since a brightness value increases sharply from the deltoid muscle 310 to the fat layer 320, an intensity gradient at a boundary between the deltoid muscle 310 and the fat layer 320 may exceed a positive threshold.

Furthermore, as a brightness value decreases sharply from the fat layer 320 to the bursa 330, a boundary between the fat layer 320 and the bursa 330 may have an intensity gradient that is less than a negative threshold.

Thus, the ultrasound apparatus 1000 may determine a first boundary 402 in the second graph 420 having an intensity gradient that is greater than or equal to the positive threshold as an upper edge of the fat layer 320. In addition, the ultrasound apparatus 1000 may determine a second boundary 403 in the second graph 420 having an intensity gradient that is less than or equal to the negative threshold as a lower edge of the fat layer 320.

A third graph 430 illustrates a width between portions respectively having positive and negative intensity gradients.

Because an upper edge of the fat layer 320 has an intensity gradient that is greater than or equal to the positive threshold while a lower edge thereof has an intensity gradient that is less than or equal to the negative threshold, the ultrasound apparatus 1000 may determine as a thickness of the fat layer 320 a width 404 between the first boundary 402 having an intensity gradient that is greater than or equal to the positive threshold and the second boundary 403 having an intensity gradient that is less than or equal to the negative threshold.

Figure 5:
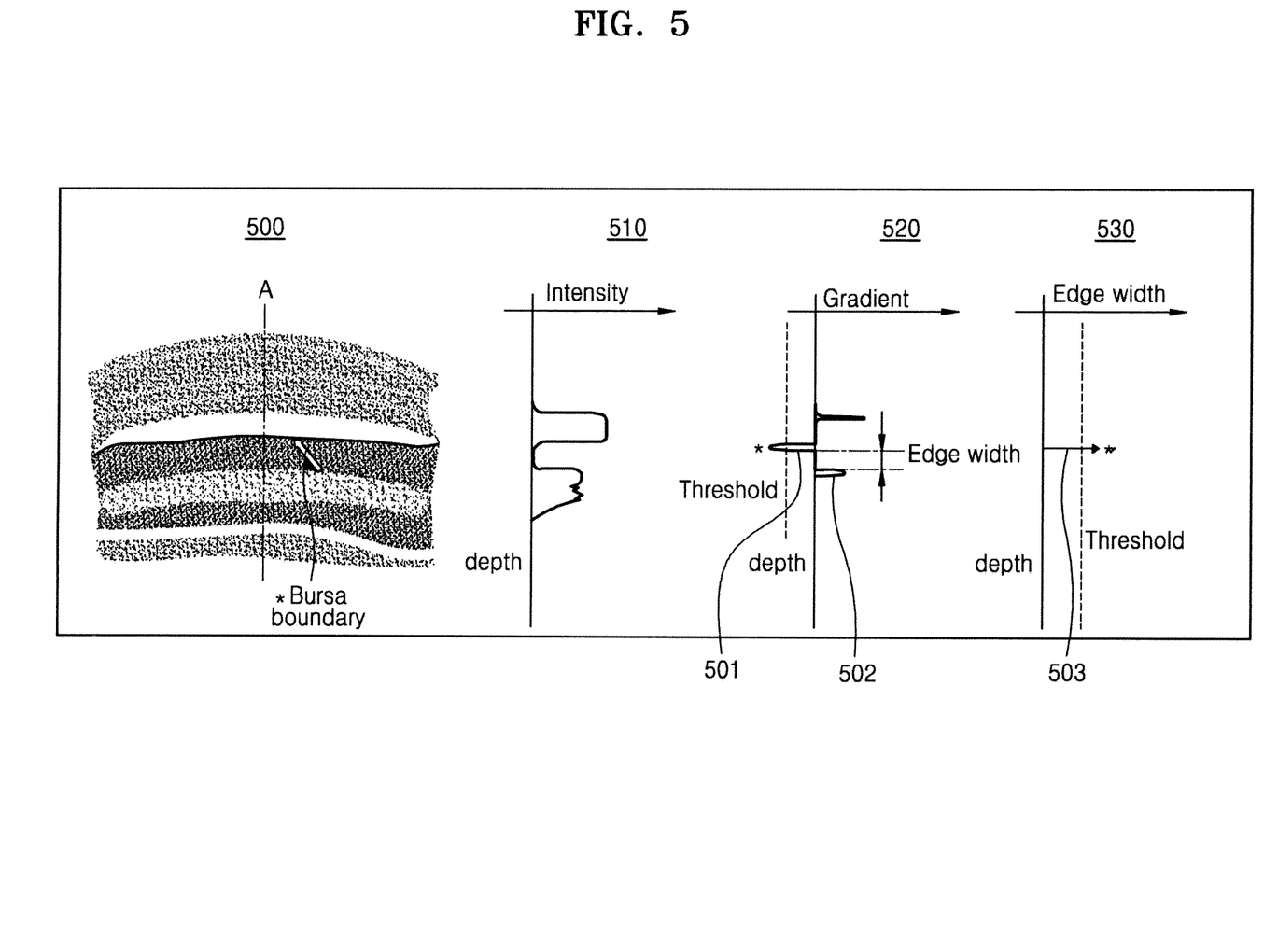
FIG. 5 illustrates detection of a thickness of a bursa according to an exemplary embodiment of the present invention.

FIG. 5 illustrates detection of a thickness of a bursa 330 according to an exemplary embodiment of the present invention.

A shoulder ultrasound image 500 shown in FIG. 5 may correspond to a shoulder ultrasound image 400 shown in FIG. 4. A fat layer 320, the bursa 330, and a supraspinatus tendon 340 will be described mainly with reference to FIG. 5.

A first graph 510 that illustrates an echo signal intensity in a direction that a depth value increases. As evident from the first graph 510, the echo signal intensity increases sharply at the fat layer 320, decreases sharply at the bursa 330, and increases again at the supraspinatus tendon 340.

A second graph 520 illustrates an intensity gradient in a direction that a depth value increases. As evident from the second graph 520, since a brightness value decreases rapidly from the fat layer 320 to the bursa 330, a boundary between the fat layer 320 and the bursa 330 may have an intensity gradient that is less than a negative threshold. Furthermore, since the brightness value increases again from the bursa 330 to the supraspinatus tendon 340, a boundary between the bursa 330 and the supraspinatus tendon 340 may have a positive intensity gradient value.

Thus, the ultrasound apparatus 1000 may determine a first boundary 501 having an intensity gradient that is less than or equal to the negative threshold as a lower edge of the fat layer 320 or an upper edge of the bursa 330. Furthermore, the ultrasound apparatus 1000 may determine a second boundary 502 disposed below the bursa 330 and having a positive intensity gradient value as a lower edge of the bursa or an upper edge of the supraspinatus tendon 340.

A third graph 530 illustrates a width between portions respectively having positive and negative intensity gradient values.

Because upper and lower edges of the bursa 330 have a negative intensity gradient and a positive intensity gradient, respectively, the ultrasound apparatus 1000 may determine as a thickness of the bursa 330 a width 503 between the first boundary 501 and the second boundary 502 respectively having a negative intensity gradient and a positive intensity gradient.

Figure 6:
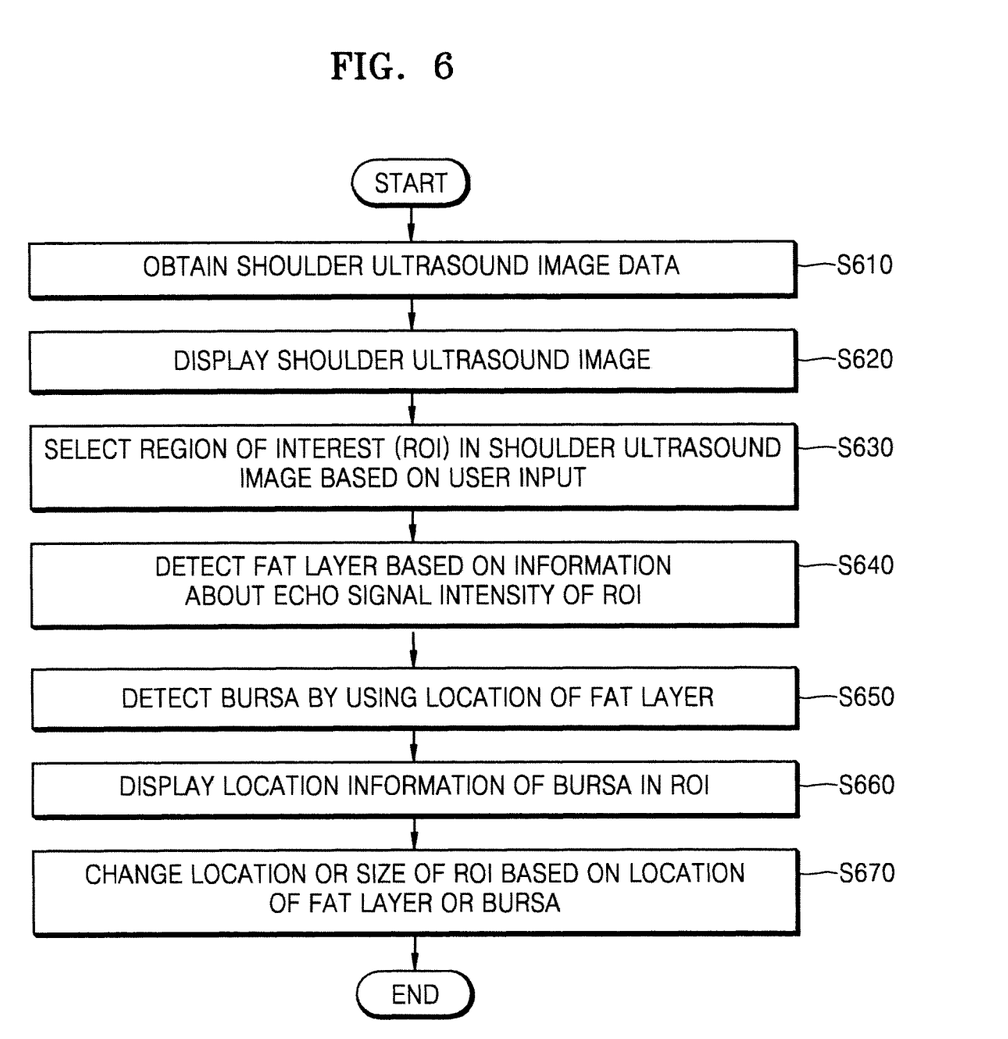
FIG. 6 is a flowchart of a method of displaying location information of a bursa in a region of interest (ROI) in an ultrasound apparatus, according to an exemplary embodiment of the present invention.

FIG. 6 is a flowchart of a method of displaying location information of a bursa in a region of interest (ROI) in the ultrasound apparatus (1000 in FIG. 1), according to an exemplary embodiment of the present invention.

The ultrasound apparatus 1000 may acquire shoulder ultrasound image data (S610). Since operation S610 corresponds to operation S210 described with reference to FIG. 2, a detailed description thereof is omitted.

The ultrasound apparatus 1000 may display the shoulder ultrasound image (300 in FIG. 3) based on the shoulder ultrasound image data (S620). According to one embodiment, the ultrasound apparatus 1000 may display the shoulder ultrasound image 300 as a 2D brightness (B) mode image. For example, as shown in FIG. 3, the shoulder ultrasound image 300 may include the deltoid muscle 310, the fat layer 320, the bursa 330, and the supraspinatus tendon 340, the bone, etc.

The ultrasound apparatus 1000 may select an ROI from the shoulder ultrasound image 300 based on a user input (S630). For example, the ultrasound apparatus 1000 may receive a user input for selecting an ROI including the deltoid muscle 310 and the supraspinatus tendon 340.

In one embodiment, various user input modes for selecting an ROI may be used. For example, a user input may be at least one of a key input, a touch input (e.g., tap, double-tap, touch and drag, flick, swipe, etc.), a voice input, a motion input, and a multi-input, but is not limited thereto.

In addition, according to one embodiment, the ROI may have various shapes such as a circle, an oval shape, a quadrangular shape, and a free curved shape, but is not limited thereto.

In one embodiment, the ultrasound apparatus 1000 may select an ROI in a semi-automatic manner. For example, the ultrasound apparatus 1000 may receive selection of a specific point from a user. The ultrasound apparatus 1000 may select an ROI having a predetermined size (e.g., 10 pixels or 5 cm$^2$) based on the specific point selected by the user. The predetermined size may be preset by the user or the ultrasound apparatus 1000.

The ultrasound apparatus 1000 may detect the fat layer 320 based on information about echo signal intensity of an ROI (S640). In this case, it is possible to shorten the time taken to detect the fat layer 320 because the ultrasound apparatus 1000 only has to analyze the acquired shoulder ultrasound image data for detection. Since operation S640 of detecting the fat layer 320 is performed by the ultrasound apparatus 1000 in the same manner as operation S220 described with reference to FIG. 2, a detailed description thereof is omitted herein.

The ultrasound apparatus 1000 may detect the bursa 330 by using a location of the fat layer 320 (S650). For example, the ultrasound apparatus 1000 may determine an anechoic zone disposed below the fat layer 320 as the bursa 330. For example, the ultrasound apparatus 1000 may determine an anechoic zone disposed below the fat layer 320 as the bursa 330. Since an echo signal reflected from the bursa 330 has a very low intensity, the bursa 330 appears dark below the fat layer 320 in the shoulder ultrasound image 300. Since operation S650 corresponds to operation S230 described with reference to FIG. 2, a detailed description thereof is omitted here.

The ultrasound apparatus 1000 may display location information of the bursa 330 in the ROI (S660). For example, the ultrasound apparatus 1000 may display an indicator having a preset shape or color at a location of the bursa 330 in the ROI. The shape of the indicator may be preset by a user or the ultrasound apparatus 1000. Furthermore, the ultrasound apparatus 1000 may display a first boundary line that distinguishes between the bursa 330 and the fat layer 330 and a second boundary line that distinguishes between the bursa 330 and the supraspinatus tendon 340. Operation S660 of displaying the location information of the bursa 330 will be described in more detail later with reference to FIGS. 8A through 8C.

The ultrasound apparatus 1000 may change a location or size of the ROI based on the location of the fat layer 320 or the bursa 330 (S670).

For example, the ultrasound apparatus 1000 may move the ROI up and down so that a vertical central point of the ROI is located at an upper edge of the fat layer 320. The ultrasound apparatus 1000 may also move the ROI so that the vertical central point of the ROI is located at a lower edge of the fat layer 320. The ultrasound apparatus 1000 may also move the ROI up and down so that the vertical central point of the ROI is located at a center of the fat layer 320. The ultrasound apparatus 1000 may also move the ROI up and down so that the vertical central point of the ROI is located at a center of an anechoic zone.

Since the ultrasound apparatus 1000 analyzes the shoulder ultrasound image data related to the ROI, the bursa 330 may not be accurately detected if the user fails to select the ROI properly. Thus, if the user selects the wrong ROI, the location or size of the ROI may be adjusted automatically in consideration of the location of the fat layer 320 or the bursa 330.

According to embodiments of the present invention, operations S610 through S670 may be performed in a different order, or some of them may be omitted.

Figure 7:
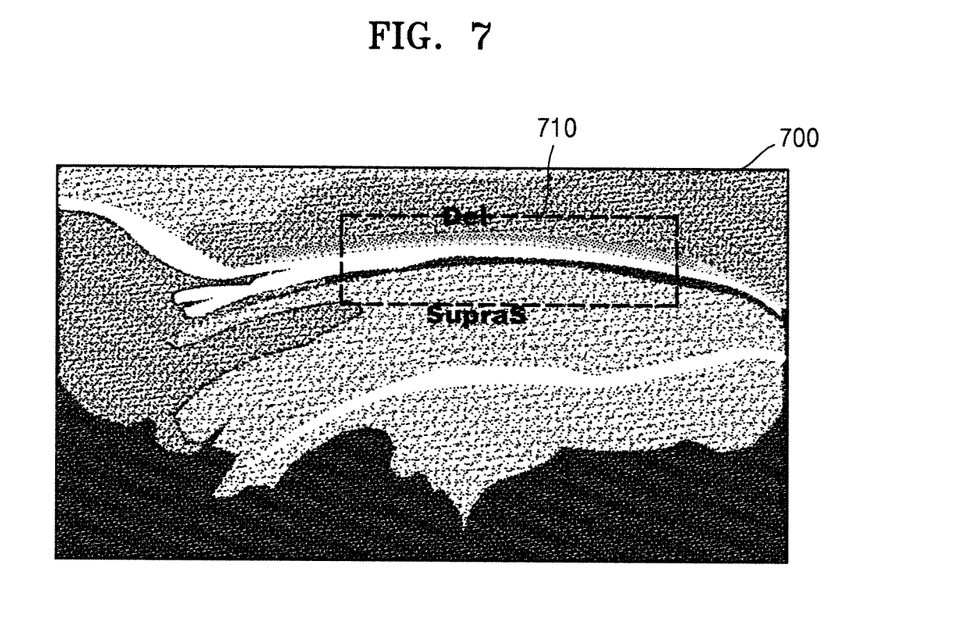
FIG. 7 illustrates an ROI according to an exemplary embodiment of the present invention.

FIG. 7 illustrates an ROI according to an exemplary embodiment of the present invention.

Referring to FIG. 7, the ultrasound apparatus (1000 in FIG. 1) may receive a user input for selecting an ROI including the deltoid muscle (310 in FIG. 4) and the supraspinatus tendon (340 in FIG. 4). In this case, the ultrasound apparatus 1000 may display an image 710 of the ROI on a shoulder ultrasound image 700.

According to one embodiment, the ultrasound apparatus 1000 may receive a user input for changing a size or location of the ROI. For example, the ultrasound apparatus 1000 may receive a request to move the image 710 or change a size of the ROI from the user.

In one embodiment, the ultrasound apparatus 1000 may detect the fat layer (320 in FIG. 4) within the ROI based on information about an echo signal intensity of the ROI. The ultrasound apparatus 1000 may also detect the bursa (330 in FIG. 3) by using a location of the fat layer 320. In this case, it is possible to shorten the time taken to detect the bursa 330 because the ultrasound apparatus 1000 only has to analyze shoulder ultrasound image data acquired within the ROI.

Figure 8A:
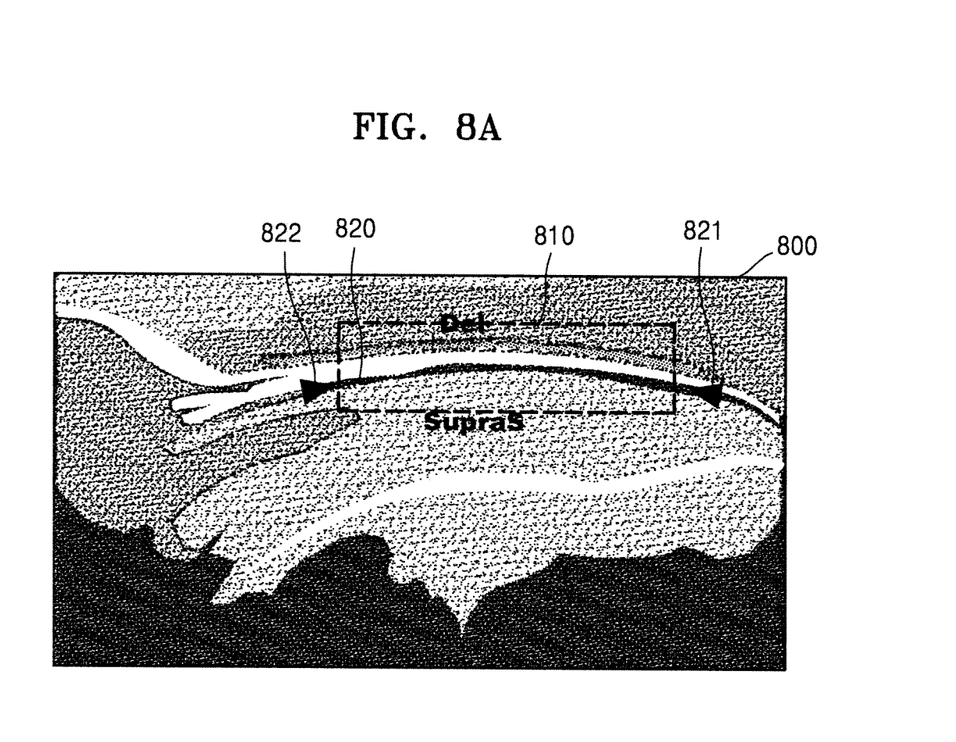
FIGS. 8A through 8C illustrate examples of displaying location information of a bursa in an ultrasound apparatus.
Figure 8B:
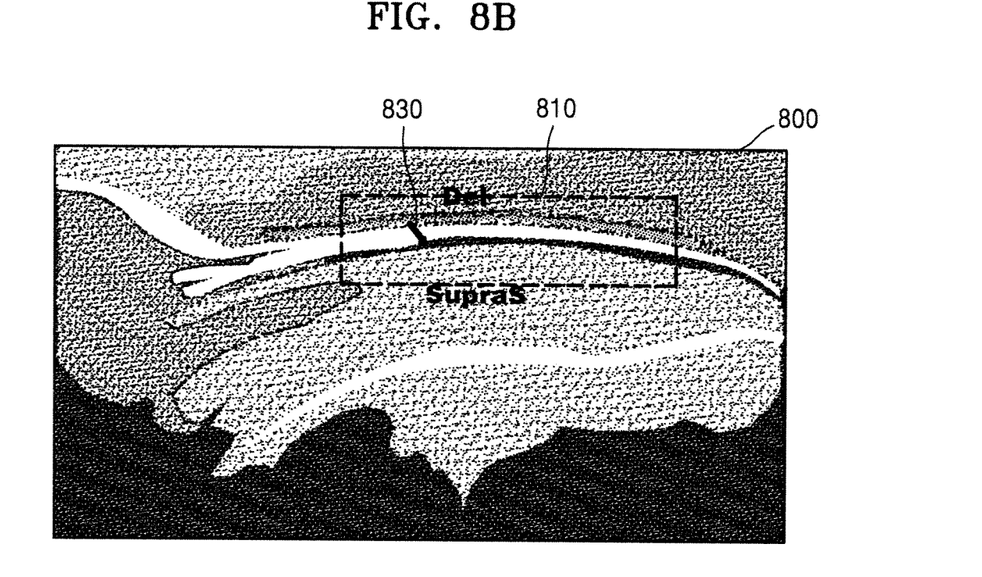
Figure 8C:
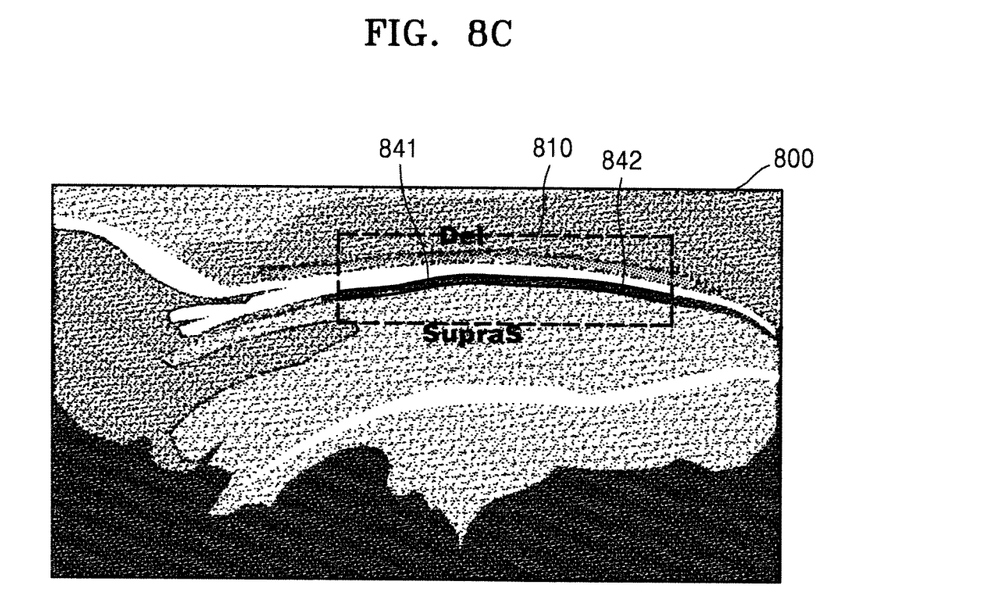

FIGS. 8A through 8C illustrate examples of displaying location information of the bursa (330 in FIG. 4) in the ultrasound apparatus (1000 in FIG. 1)

According to one embodiment, as shown in FIG. 8A, the ultrasound apparatus 1000 may display an image that is used to distinguish the bursa 300 located in an ROI 810. For example, the ultrasound apparatus 1000 may provide location information of the bursa 330 by displaying triangular images 821 and 822 on right and left sides of the bursa 330, respectively.

In another embodiment, as illustrated in FIG. 8B, the ultrasound apparatus 1000 may display an arrow image 830 on a shoulder ultrasound image 800 in an overlapping manner so as to distinguish the bursa 330 in the ROI 810.

In another embodiment, as illustrated in FIG. 8C, in order to distinguish the bursa 330 in the ROI 810, the ultrasound apparatus 1000 may display a first boundary 841 between the bursa 330 and the fat layer 320 and a second boundary 842 between the bursa 330 and the supraspinatus tendon 340 in a preset color (e.g., red) or in a preset shape (e.g., a dot-dashed line). In this case, the first boundary 841 and the second boundary 842 may represent upper and lower edges of the bursa 330, respectively.

While the ultrasound apparatus 1000 displays the location of the bursa 330 by using the triangular images 821 and 822, the arrow image 830, and the first and second boundaries 841 and 842, embodiments of the present invention are not limited thereto.

Figure 9:
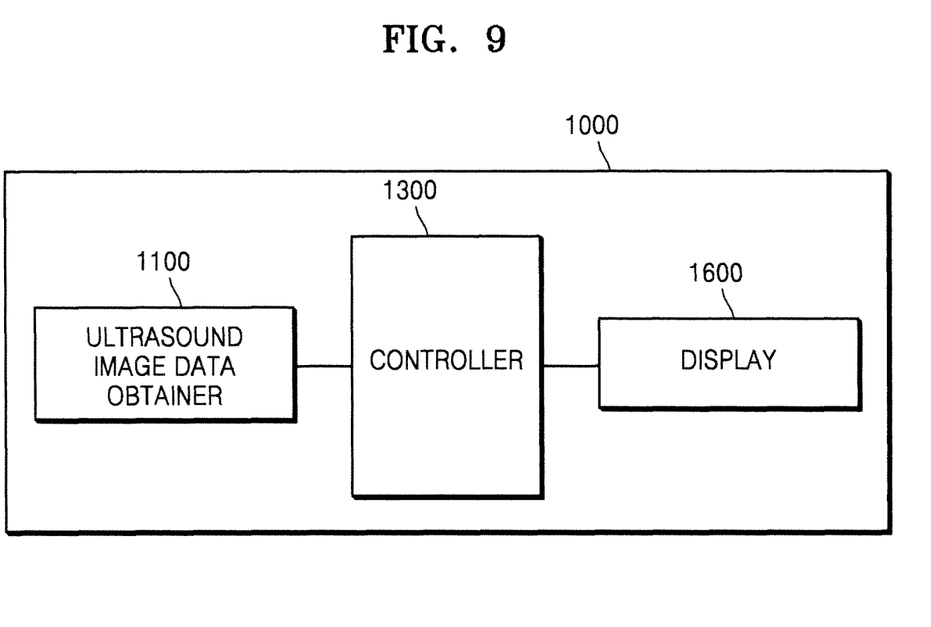
FIGS. 9 and 10 are block diagrams of a configuration of an ultrasound apparatus according to an exemplary embodiment of the present invention.
Figure 10:
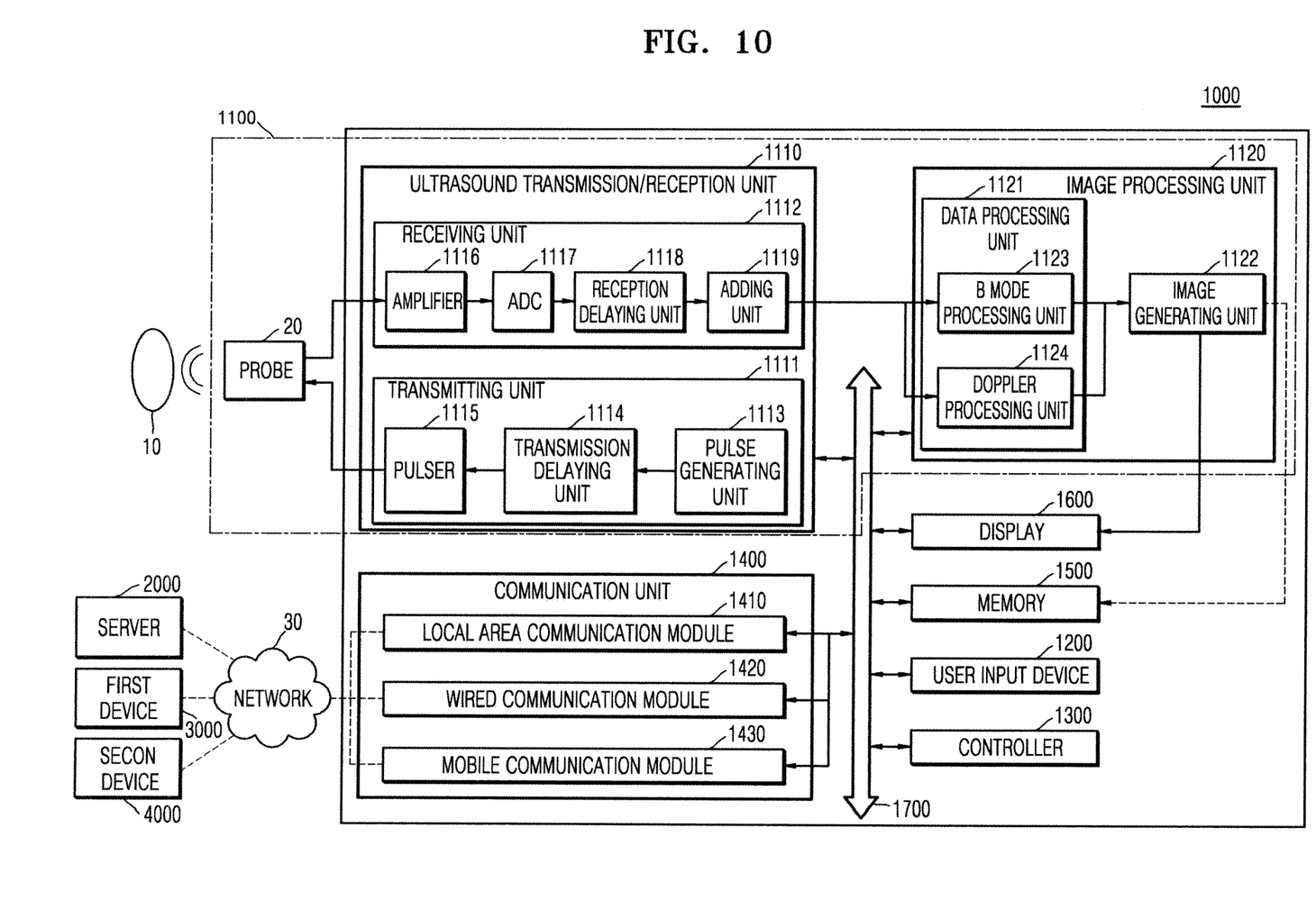

FIGS. 9 and 10 are block diagrams of a configuration of an ultrasound apparatus 1000 according to an exemplary embodiment of the present invention.

Referring to FIG. 9, the ultrasound apparatus 1000 according to the present embodiment includes an ultrasound image data obtainer 1100, a controller 1300, and a display 1600. However, the components illustrated in FIG. 9 are not essential components. The ultrasound apparatus 1000 may be realized by fewer or more components than those illustrated in FIG. 9. For example, the ultrasound apparatus 1000 may further include a user input device 1200, a communication unit 1400, and a memory 1500. The components may be connected to one another via buses 1700.

The components will now be described in detail.

The ultrasound image data obtainer 1100 may acquire ultrasound image data related to an object 10. The ultrasound image data may be a 2D or 3D ultrasound image data.

Referring to FIG. 10, the ultrasound image data obtainer 1100 may include a probe 20, an ultrasound transmission/reception unit 1110, and an image processing unit 1120.

The probe 20 transmits ultrasound signals to the object 10, based on a driving signal applied by the ultrasound transmission/reception unit 1110, and receives echo signals reflected from the object 10. The probe 20 includes a plurality of transducers that oscillate based on electric signals transmitted thereto and generate acoustic energy, that is, ultrasound waves. Furthermore, the probe 20 may be connected to a main body of the ultrasound diagnostic device 1000 by wires or wirelessly. According to embodiments of the present invention, the ultrasound apparatus 1000 may include a plurality of probes 20. According to one embodiment, the probe 20 may include at least one of a 1D probe, a 2D (matrix) probe, and a 3D probe.

A transmission unit 1111 supplies a driving signal to the probe 20 and includes a pulse generating unit 1113, a transmission delaying unit 1114, and a pulser 1115. The pulse generating unit 1113 generates pulses for forming transmission ultrasound waves based on a predetermined pulse repetition frequency (PRF), and the transmission delaying unit 1114 applies a delay time for determining transmission directionality to the pulses. Pulses, to which a delay time is applied, correspond to a plurality of piezoelectric vibrators included in the probe 20, respectively. The pulser 1115 applies a driving signal (or a driving pulse) to the probe 20 at a timing corresponding to each pulse to which a delay time is applied.

A reception unit 1112 generates ultrasound data by processing echo signals received from the probe 20. The reception unit 1112 may include an amplifier 1116, an analog-to-digital converter (ADC) 1117, a reception delaying unit 1118, and a summing unit 1119. The amplifier 1116 amplifies echo signals in each channel, and the ADC 1117 performs analog-to-digital conversion on the amplified echo signals. The reception delaying unit 1118 applies delay times for determining reception directionality to the echo signals subjected to the analog-to-digital conversion, and the summing unit 1119 generates ultrasound data by summing the echo signals processed by the reception delaying unit 1118. For example, the summing unit 1119 may generate shoulder ultrasound image data. Furthermore, the summing unit 1119 may acquire the shoulder ultrasound image data in real-time during injection of a medicine into the bursa (330 in FIG. 3) via a syringe.

The image processing unit 1120 generates an ultrasound image by scan-converting ultrasound data generated by the ultrasound transmission/reception unit 1110 and displays the ultrasound image. In addition, an ultrasound image may include not only a gray-scale ultrasound image obtained by scanning an object in an amplitude (A) mode, a B mode, and a motion (M) mode, but also a Doppler image representing a moving object by using a Doppler effect. The Doppler image may include a blood flow Doppler image (also called a color Doppler image) showing flow of blood, a tissue Doppler image showing movement of tissue, and a spectral Doppler image showing a moving speed of an object as a waveform.

A B mode processing unit 1123 extracts B mode components from ultrasound image data and processes the B mode components. An image generating unit 1122 may generate a B mode image indicating signal intensities as brightness based on the extracted B mode components. For example, the image generating unit 1122 may generate a shoulder ultrasound image including the deltoid muscle (310 in FIG. 3), the fat layer (320 in FIG. 3), the bursa 330, and the supraspinatus tendon (340 in FIG. 3) as a 2D B mode image.

The image generating unit 1122 may sequentially generate a plurality of B mode images, e.g., first and second B mode images. The image generating unit 1122 may also generate a real-time shoulder ultrasound image during injection of a medicine into the bursa 330 through a syringe.

A Doppler processing unit 1124 may extract Doppler components from ultrasound image data, and the image generating unit 1122 may generate a Doppler image indicating movement of an object as colors or waveforms based on the extracted Doppler components.

According to one embodiment, the image generating unit 1122 may generate a 3D ultrasound image via volume-rendering of volume data and an elasticity image which shows the degree of deformation of the object 10 due to pressure. In addition, the image generating unit 1122 may estimate a movement path of a speckle from ultrasound image data and generate a speckle tracking image that shows movement of the speckle as an arrow or color based on the movement path of the speckle.

Furthermore, the image generating unit 1122 may display additional information in an ultrasound image by using text and graphics. For example, the image generating unit 1122 may add at least one annotation related to the whole or a part of an ultrasound image to the ultrasound image. In other words, the image generating unit 1122 may analyze an ultrasound image and recommend at least one annotation related to the whole or a part of the ultrasound image based on the result of analysis. The image generating unit 1122 may also add at least one annotation selected by a user to an ultrasound image.

In addition, the image processing unit 1120 may extract an ROI from an ultrasound image by using an image processing algorithm. In this case, the image processing unit 1120 may add a color, a pattern, or a line to the ROI.

The user input device 1200 is a means via which a user (e.g., a sonographer) inputs data for controlling the ultrasound apparatus 1000. For example, the user input device 1200 may include a key pad, a dome switch, a touch pad (capacitive overlay, resistive overlay, infrared beam, surface acoustic wave, integral strain gauge, piezoelectric, etc.), a track ball, and a jog switch, but is not limited thereto. The user input device 1200 may further include various other input elements such as an electrocardiogram measuring module, a respiration measuring module, a voice recognition sensor, a gesture recognition sensor, a fingerprint recognition sensor, an iris recognition sensor, a depth sensor, a distance sensor, etc.

According to one embodiment, the user input device 1200 may detect a real touch and a proximity touch. The user input device 1200 may detect a touch input (e.g., touch & hold, tap, double tap, flick, etc.) on an ultrasound image. The user input device 1200 may also detect a drag input from a point where the touch input is detected. In addition, the user input device 1200 may detect a multi-touch input (e.g., pinch) on at least two points in the ultrasound image.

According to one embodiment, the user input device 1200 may receive an ROI selected in a B mode image. For example, the user input device 1200 may receive a user input for selecting an ROI, including the deltoid muscle 310 and the supraspinatus tendon 340, in a shoulder ultrasound image.

The controller 1300 may control overall operations of the ultrasound apparatus 1000. For example, the controller 1300 may control overall operations of the ultrasound image data obtainer 1100, the user input device 1200, the communication unit 1400, the memory 1500, and the display 1600.

The controller 1300 may detect the fat layer 320 located between the deltoid muscle 310 and the supraspinatus tendon 340, based on information about an echo signal intensity contained in shoulder ultrasound image data.

For example, the controller 1300 may detect a region having an echo signal intensity that is greater than or equal to a threshold value as the fat layer 320. The controller 1300 may determine a first boundary in a shoulder ultrasound image having an echo signal intensity gradient that is greater than or equal to a positive first threshold and a second boundary having an echo signal intensity gradient that is less than or equal to a negative second threshold as an upper edge and a lower edge of the fat layer 320, respectively. In addition, the controller 1300 may detect a thickness of the fat layer 320 based on a distance between the first and second boundaries.

The controller 1300 may detect the bursa 330 located between the fat layer 320 and the supraspinatus tendon 340 by using a location of the fat layer 320. For example, the controller 1300 may determine an anechoic zone disposed below the fat layer 320 as the bursa 330.

The controller 1300 may further extract from the shoulder ultrasound image a third boundary having an echo signal intensity gradient that is less than the positive first threshold and greater than a third threshold and determine the third boundary as an upper edge of the supraspinatus tendon 340. In this case, the controller 1300 may also detect a thickness of the bursa 330 based on a distance between the second and third boundaries.

If an ROI is selected, the controller 1300 may detect the fat layer 320 based on information about an echo signal intensity of the ROI. The controller 1300 may change a location or size of the ROI based on the location of the fat layer 320 or the bursa 330.

The communication unit 1400 may include at least one component that enables communication between the ultrasound apparatus 1000 and one of a server 2000, a first device 3000, and a second device 4000. For example, the communication unit 1400 may further include a local area communication module 1410, a wired communication module 1420, and a mobile communication module 1430.

The local area communication module 1410 is a module for performing local area communication with a device within a predetermined distance. Examples of local area communication technology include wireless Local Area Networks (WLAN/Wi-Fi), Bluetooth, Bluetooth Low Energy (BLE), Ultra Wideband (UWB), ZigBee, Near Field Communication (NFC), Wi-Fi Direct (WFD), Infrared Data Association (IrDA), etc.

The wired communication module 1420 is a module for performing communication by using an electric signal or an optical signal. Examples of wired communication technology include wired communication technologies using a pair cable, a coaxial cable, an optical fiber cable, and an Ethernet cable.

The mobile communication module 1430 transmits or receives wireless signals to or from at least one of a base station, the first and second devices 3000 and 4000, and the server 2000 on a mobile communication network. Here, the wireless signals may include voice call signals, video call signals, or various types of data for transmission and reception of text/multimedia messages.

The communication unit 1400 is connected to a network 30 by wires or wirelessly and communicates with an external device such as the first device 3000, the second device 4000, or the server 2000. The communication unit 1400 may exchange data with a hospital server or another medical device in a hospital that is connected via a Picture Archiving and Communications System (PACS). Furthermore, the communication unit 300 may perform data communication according to the Digital Imaging and Communications in Medicine (DICOM) standard.

The communication unit 1400 may transmit or receive data related to diagnosis of the object 10, e.g., an ultrasound image, ultrasound image data, and Doppler image data of the object 10, via the network 30. The communication unit 1400 may also transmit or receive medical images obtained by other medical devices, such as a CT image, an MR image, and an X-ray image. Furthermore, the communication unit 1400 may receive information related to a diagnosis history or a treatment schedule of a patient from the server 2000 and utilizes the information for diagnosing the patient.

The memory 1500 may store programs for processing by the controller 1300 and data that is input or output, such as ultrasound image data, information about a boundary of medicine diffusion, examinee information, probe information, a body marker, etc.).

The memory 1500 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable ROM (EEPROM), PROM, magnetic memory, a magnetic disc, and an optical disc. The ultrasound apparatus 1000 may utilize a web storage or a cloud server that functions as the memory 1500 on the Internet.

The display 1600 displays and outputs information processed by the ultrasound apparatus 1000. For example, the display 1600 may display an ultrasound image or a user interface (UI) or graphical user interface (GUI) related to a control panel.

According to one embodiment, the display 1600 may display location information of the bursa 330 on a shoulder ultrasound image generated based on shoulder ultrasound image data. For example, the display 1600 may display an indicator having a preset shape at a location of the bursa 330 in the shoulder ultrasound image. The display 1600 may display a first boundary line that distinguishes the bursa 330 from the fat layer 320 and a second boundary line that distinguishes the bursa 330 from the supraspinatus tendon 340.

When the display 1600 and a touch pad form a layer structure to form a touch screen, the display 1600 may be used as an input device as well as an output device. The display 1600 may include at least one of a liquid crystal display (LCD), a thin film transistor-LCD (TFT-LCD), an organic light-emitting diode (OLED) display, a flexible display, a 3D display, and an electrophoretic display. The ultrasound apparatus 1000 may include two or more displays 1600 according to embodiments of the present invention.

Methods of displaying location information of a bursa, according to embodiments of the present invention, can be implemented through program instructions that can be executed by various computer means and be recorded on computer-readable recording media. The computer-readable recording media may include individual or a combination of program instructions, data files, and data structures. The program instructions being recorded on the computer-readable recording media can be specially designed or constructed for the present invention or are known to and used by a person skilled in the art of computer software. Examples of the computer readable recording media include magnetic media (e.g., hard disks, floppy disks, magnetic tapes, etc.), optical recording media (e.g., CD-ROMs, DVDs, etc.), magneto-optical media such as floptical disks, and hardware devices specially configured to store and perform program instructions (ROM, RAM, flash memories, etc.). Examples of program instructions include machine language codes produced by a compiler and high-level language codes that can be executed by a computer using an interpreter.

The ultrasound apparatus 1000 according to an embodiment of the present invention allows a user to accurately and easily identify a location of a bursa, thereby facilitating insertion of a syringe into the bursa during medicine treatment and maximizing the effect of treatment of a shoulder.

The ultrasound apparatus 1000 is also configured to accurately measure a thickness of the bursa, thereby allowing efficient follow-up examination.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of displaying location information of a bursa, the method comprising:
obtaining, by an ultrasound apparatus, shoulder ultrasound image data;
selecting, by the ultrasound apparatus, a region of interest (ROI) including a deltoid muscle and a tendon in the shoulder ultrasound image data, based on a user input;
detecting, by the ultrasound apparatus, a fat layer located between the deltoid muscle and the tendon, based on information about an intensity of an echo signal contained in the shoulder ultrasound image data from the ROI;
detecting, by the ultrasound apparatus, the bursa located between the fat layer and the tendon by using a location of the fat layer;
displaying, by the ultrasound apparatus, the location information of the bursa on a shoulder ultrasound image generated based on the shoulder ultrasound image data;

changing, by a controller in the ultrasound apparatus, when the bursa is not detected in the ROI selected based on the user input, a location or size of the ROI based on the location of the fat layer or the bursa, wherein the changing the location or size of the ROI comprises changing, based on the location of the fat layer or the bursa, the location of the ROI so that a vertical central point of the ROI is located at a predetermined point in the location of the fat layer or at a center of an anechoic zone near the fat layer, wherein the displaying the location information of the bursa comprises:

displaying the location information of the bursa on a real-time shoulder ultrasound image obtained in real-time according to injection of a medicine into the bursa; and displaying a thickness of the bursa, determined based on a boundary having a negative intensity gradient for upper edges of the bursa and a boundary having a positive intensity gradient for lower edges of the bursa.

2. The method of claim 1, wherein the detecting of the fat layer comprises detecting a region having the intensity of the echo signal that is greater than or equal to a threshold value as the fat layer.

3. The method of claim 1, wherein the detecting of the fat layer comprises:

detecting a first boundary having an intensity gradient of the echo signal that is greater than or equal to a positive first threshold in the shoulder ultrasound image; and determining the first boundary as an upper edge of the fat layer.

4. The method of claim 3, wherein the detecting of the fat layer further comprises:

detecting a second boundary having an intensity gradient of the echo signal that is less than or equal to a negative second threshold in the shoulder ultrasound image; and determining the second boundary as a lower edge of the fat layer.

5. The method of claim 4, wherein the detecting of the fat layer further comprises detecting a thickness of the fat layer based on a distance between the first and second boundaries.

6. The method of claim 1, wherein the detecting of the bursa comprises determining the anechoic zone disposed below the detected fat layer as the bursa.

7. The method of claim 4, wherein the displaying of the location information of the bursa further comprises:

detecting a third boundary having an intensity gradient of the echo signal that is less than the positive first threshold and is greater than a third threshold in the shoulder ultrasound image; and determining the third boundary as an upper edge of the tendon.

8. The method of claim 7, wherein the displaying of the location information of the bursa further comprises detecting the thickness of the bursa based on a distance between the second and third boundaries.

9. The method of claim 1, wherein the displaying of the location information of the bursa comprises displaying an indicator having a preset shape at a location of the bursa on the shoulder ultrasound image.

10. The method of claim 1, wherein the displaying of the location information of the bursa comprises marking a first boundary line that distinguishes the bursa from the fat layer and a second boundary line that distinguishes the bursa from the tendon.

11. The method of claim 1, wherein the displaying of the location information of the bursa on the real-time shoulder ultrasound image comprises:

obtaining shoulder ultrasound image data in real-time during injection of the medicine into the bursa through a syringe; and displaying the location information of the bursa on the real-time shoulder ultrasound image by using the shoulder ultrasound image data.

12. A non-transitory computer-readable recording medium having recorded thereon a program, when executed by a computer, causing the computer to perform:

obtaining shoulder ultrasound image data;

selecting a region of interest (ROI) including a deltoid muscle and a tendon in the shoulder ultrasound image data, based on a user input;

detecting a fat layer located between the deltoid muscle and the tendon, based on information about an intensity of an echo signal contained in the shoulder ultrasound image data from the ROI;

detecting a bursa located between the fat layer and the tendon by using a location of the fat layer;

displaying location information of the bursa on a shoulder ultrasound image generated based on the shoulder ultrasound image data; and changing, when the bursa is not detected in the ROI selected based on the user input, a location or size of the ROI based on the location of the fat layer or the bursa, wherein the changing the location or size of the ROI comprises:

changing, based on the location of the fat layer or the bursa, the location of the ROI so that a vertical central point of the ROI is located at a predetermined point in the location of the fat layer or at a center of an anechoic zone near the fat layer, wherein the displaying the location information of the bursa comprises:

displaying the location information of the bursa on a real-time shoulder ultrasound image obtained in real-time according to injection of a medicine into the bursa; and displaying a thickness of the bursa, determined based on a boundary having a negative intensity gradient for upper edges of the bursa and a boundary having a positive intensity gradient for lower edges of the bursa.

* * * * *